United States Patent
Lu et al.

(10) Patent No.: US 11,394,139 B2
(45) Date of Patent: *Jul. 19, 2022

(54) THIN-FILM CONNECTORS FOR DATA ACQUISITION SYSTEM

(71) Applicant: Verily Life Sciences LLC, South San Francisco, CA (US)

(72) Inventors: Bo Lu, Santa Clara, CA (US); Annapurna Karicherla, Cupertino, CA (US); Huanfen Yao, Brisbane, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/122,448

(22) Filed: Dec. 15, 2020

(65) Prior Publication Data

US 2021/0098909 A1 Apr. 1, 2021

Related U.S. Application Data

(63) Continuation of application No. 16/734,729, filed on Jan. 6, 2020, now Pat. No. 10,892,573.

(Continued)

(51) Int. Cl.
*H01R 12/53* (2011.01)
*H01R 13/04* (2006.01)
(Continued)

(52) U.S. Cl.
CPC .......... *H01R 12/53* (2013.01); *A61N 1/3752* (2013.01); *H01R 13/04* (2013.01); *H01R 13/10* (2013.01);
(Continued)

(58) Field of Classification Search
CPC ........ H01R 12/53; H01R 12/78; H01R 12/79; H01R 13/04; H01R 13/10; H01R 2201/12; A61N 1/3752
See application file for complete search history.

(56) References Cited

U.S. PATENT DOCUMENTS 4,526,432 A 7/1985 Cronin et al.
5,383,788 A 1/1995 Spencer
(Continued)

FOREIGN PATENT DOCUMENTS

WO 2018089895 5/2018

*Primary Examiner* — Harshad C Patel
(74) *Attorney, Agent, or Firm* — Kilpatrick Townsend & Stockton LLP

(57) ABSTRACT

Thin film connectors are described for connecting a lead assembly and a data acquisition system. Particularly, a connector includes a button having a housing and conductive pins extending from a proximal end of the housing through a base plate into a cavity on a distal end of the housing. The connector further includes a thin-film adapter having: (i) a supporting structure, (ii) bond pads formed on the supporting structure, (iii) a cable having conductive traces electrically connected to the bond pads, and (iv) feedthroughs that pass through the supporting structure and are electrically connected with the bond pads. Each conductive pin extends through a feedthrough, and each conductive pin is in electrical connection with one or more conductive traces via each bond pad.

12 Claims, 12 Drawing Sheets

Related U.S. Application Data

(60) Provisional application No. 62/788,525, filed on Jan. 4, 2019.

(51) Int. Cl.
    *A61N 1/375*     (2006.01)
    *H01R 13/10*     (2006.01)
    *H01R 12/78*     (2011.01)
    *H01R 12/79*     (2011.01)

(52) U.S. Cl.
    CPC .............. *H01R 12/78* (2013.01); *H01R 12/79* (2013.01); *H01R 2201/12* (2013.01)

(56) References Cited

U.S. PATENT DOCUMENTS

| | | |
|---|---|---|
| 5,862,803 A | 1/1999 | Besson et al. |
| 6,321,126 B1 | 11/2001 | Kuzma |
| 6,662,035 B2 | 12/2003 | Sochor |
| 7,168,989 B2 | 1/2007 | Faulkner |
| 7,794,256 B1 | 9/2010 | Sochor |
| 8,142,200 B2 | 3/2012 | Crunkilton et al. |
| 8,317,524 B2 | 11/2012 | Bailey |
| 8,369,957 B2 | 2/2013 | Greenberg et al. |
| 8,956,166 B2 | 2/2015 | Ritner |
| 9,059,532 B2 | 6/2015 | Hermannsson |
| 9,093,801 B2 | 7/2015 | Williams et al. |
| 9,452,104 B2 | 9/2016 | Greiner et al. |
| 9,992,892 B2 | 6/2018 | Baeumel et al. |
| 10,892,573 B1 * | 1/2021 | Lu .......................... A61B 5/273 |
| 2007/0167089 A1 | 7/2007 | Gobron et al. |
| 2012/0149230 A1 | 6/2012 | Dove |
| 2015/0380815 A1 | 12/2015 | Boutayeb et al. |
| 2016/0087598 A1 | 3/2016 | Thom et al. |
| 2018/0241163 A1 | 8/2018 | Piromalli |
| 2018/0333571 A1 | 11/2018 | Pepin et al. |

\* cited by examiner

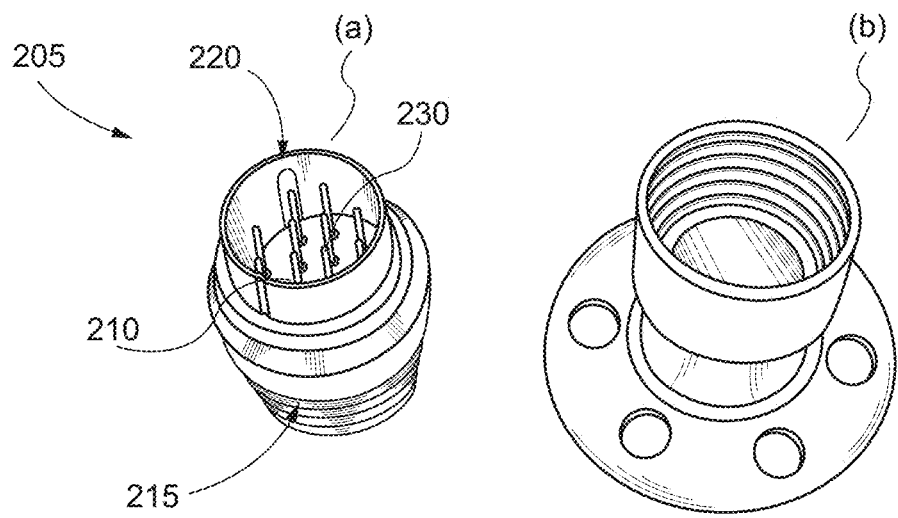
FIG. 2A
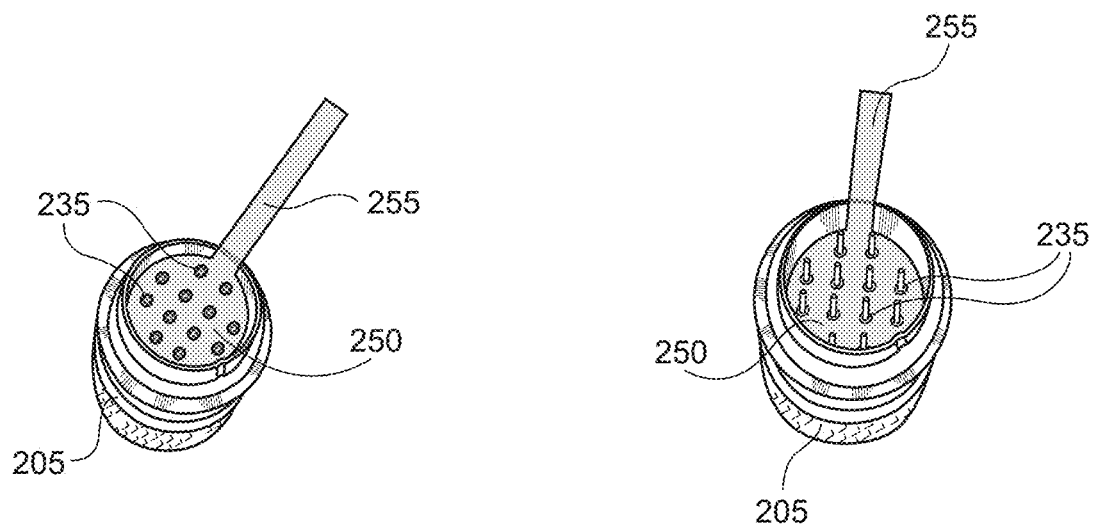
FIG. 2B
FIG. 2C

THIN-FILM CONNECTORS FOR DATA ACQUISITION SYSTEM

CROSS-REFERENCE TO RELATED APPLICATION

The present application is a continuation of U.S. patent application Ser. No. 16/734,729 filed Jan. 6, 2020, which claims the benefit of priority to U.S. Provisional Application No. 62/788,525, filed Jan. 4, 2019, the entire contents of which are incorporated by reference herein for all purposes.

FIELD OF THE INVENTION

The present disclosure relates to data acquisition, and in particular to thin film connectors between a lead assembly and a data acquisition system.

BACKGROUND

Data acquisition (DAQ) is the process of measuring an electrical or physical phenomenon such as voltage, current, temperature, pressure, or sound with a computer. A DAQ system comprises sensors (e.g., recording electrodes), DAQ measurement hardware, and a computer with programmable software. Typically, the sensors are connected to the electronics (e.g., the hardware and software) via a lead assembly. The lead assembly is typically formed of a conductive material and takes the form of an insulated wire (e.g., a dedicated channel) connected to the sensors via a first connector on one end (e.g., a distal end) and the electronics of the via a second connector on another end (e.g., a proximal end). In some instances (e.g., deep implants), the lead assembly comprises additional conductors and connectors such as extension wires or a cable connected via connectors between the sensors and the electronics of the neurostimulator.

Conventional DAQ systems include between four and sixteen sensors or electrodes, and thus typically include four to sixteen channels or wires connected respectively to the sensors at the distal end and the electronics at the proximal end. However, there is a need for high density interfaces that include greater than sixteen sensors to interface with larger tissue volumes, to recruit smaller populations of neurons for recording. Increasing the density or number of sensors can increase the number of channels or wires needed to connect the sensors and the electronics of the DAQ systems. In order to implement high channel or wire counts, there is a need for reliable electrical connections that can maintain contact and electrical isolation in a subject body (e.g., a patient body). Standard connectors for DAQ systems either terminate with male pins or female solder cups. Direct soldering, welding or mechanical crimping with the male pins or female solder cups may work for low channel counts (e.g., bipolar or tripolar design), but become infeasible when there are much denser contacts. Therefore, there is a need for reliable connectors for lead assemblies having high density interfaces.

BRIEF SUMMARY

In various embodiments, a connector is provided that comprises: a button comprising: a housing comprising: a proximal end, a distal end, a cavity, and a base plate positioned in the cavity separating the proximal end and the distal end; and a plurality of conductive pins extending from the proximal end of the housing through the base plate, and extending into a portion of the cavity on the distal end of the housing. The connector further comprises a thin-film adapter comprising: a supporting structure comprising a main body and a cable. The main body is positioned within the portion of the cavity on the distal end of the housing. The thin-film adapter further comprises a plurality of bond pads formed on the main body, and a plurality of conductive traces formed on the cable and extending onto the main body. The one or more traces of the plurality of conductive traces terminate at each bond pad of the plurality of bond pads. The thin-film adapter further comprises a plurality of feedthroughs that pass through the plurality of bond pads and the main body. Each conductive pin of the plurality of conductive pins extends through a feedthrough of the plurality of conductive feedthroughs, and each conductive pin is in electrical connection with the one or more traces of the plurality of conductive traces via each bond pad of the plurality of bond pads.

In some embodiments, the supporting structure is comprised of one or more layers of dielectric material, and the dielectric material is polyimide, liquid crystal polymer, parylene, polyether ether ketone, or a combination thereof. In some embodiments, the plurality of conductive traces are comprised of one or more layers of conductive material, and the conductive material is platinum (Pt), platinum/iridium (Pt/Ir), titanium (Ti), gold/titanium (Au/Ti), or any alloy thereof. In some embodiments, the plurality of bond pads are comprised of one or more layers of conductive material, and the conductive material is gold (Au), platinum (Pt), platinum/iridium (Pt/Ir), titanium (Ti), gold/titanium (Au/Ti), or any alloy thereof.

In some embodiments, the cable extends from the cavity to an environment exterior of the button In some embodiments, the main body of the supporting structure and the cable of the supporting structure are monolithic. In other embodiments, the main body of the supporting structure and the cable of the supporting structure are separate structures.

In some embodiments, the thin-film adapter further comprises pressure sensitive adhesive that attaches the main body to the base plate.

In some embodiments, the thin-film adapter further comprises a conductive epoxy disposed on a bottom of each conductive pin of the plurality of conductive pins and each bond pad of the plurality of bond pads, respectively, to electrically connect each conductive pin to a corresponding bond pad.

In some embodiments, the thin-film adapter further comprises an insulation layer formed over the main body of the supporting structure and at least a portion of each bond pad of the plurality of bond pads.

In some embodiments, the thin-film adapter further comprises a backfill layer formed over the main body of the supporting structure and fills a majority of a volume of the cavity of the housing.

In various embodiments, a connector is provided that comprises: a button comprising: a housing comprising: a proximal end, a distal end, a cavity, and a base plate positioned in the cavity separating the proximal end and the distal end; and a plurality of conductive pins extending from the proximal end of the housing through the base plate, and extending into a portion of the cavity on the distal end of the housing. The connector further comprises a thin-film adapter comprising: a supporting structure positioned within the portion of the cavity on the distal end of the housing; a plurality of bond pads formed on the supporting structure; a plurality of conductive feedthroughs that pass through the supporting structure and are electrically connected to the plurality of bond pads; and a cable comprising a plurality of conductive traces that are electrically connected with the plurality of bond pads. Each conductive pin of the plurality of conductive pins extends through a conductive feedthrough of the plurality of feedthroughs, and each conductive pin is in electrical connection with a trace of the plurality of conductive traces via a bond pad of the plurality of bond pads.

In some embodiments, the supporting structure is comprised of one or more layers of dielectric material, and the dielectric material is polyimide, liquid crystal polymer, parylene, polyether ether ketone, or a combination thereof. In some embodiments, the plurality of conductive traces are comprised of one or more layers of conductive material, and the conductive material is platinum (Pt), platinum/iridium (Pt/Ir), titanium (Ti), gold/titanium (Au/Ti), or any alloy thereof. In some embodiments, the plurality of bond pads are comprised of one or more layers of conductive material, and the conductive material is gold (Au), platinum (Pt), platinum/iridium (Pt/Ir), titanium (Ti), gold/titanium (Au/Ti), or any alloy thereof.

In some embodiments, the cable extends from the cavity to an environment exterior of the button. In some embodiments, the supporting structure and the cable are monolithic. In other embodiments, the supporting structure and the cable are separate structures.

In some embodiments, the plurality of conductive traces are electrically connected with the plurality of bond pads via an anisotropic conductive film or anisotropic conductive paste. In some embodiments, a bond formed between each trace of the plurality of conductive traces and each bond pad of the plurality of bond pads is encapsulated in an insulator. Optionally, the insulator is silicone.

In some embodiments, the button further comprises a spring positioned over the supporting structure and the base plate within the portion of the cavity on the distal end of the housing; and a cap over a portion of the housing that holds the spring under compression within the portion of the cavity on the distal end of the housing, where the spring holds the supporting structure abutted against the base plate. Optionally, an outer diameter of the spring matches an inner diameter of the housing, and the spring is positioned in direct contact with the supporting structure. In certain embodiments, the adapter is removable from the button.

In various embodiments, a connector is provided that comprises: a button comprising: a housing comprising a proximal end, a distal end, and a base plate formed at the distal end; and a plurality of conductive cups formed on the base plate. The button further comprises: a thin-film adapter comprising: a supporting structure comprising a first side and a second side, where the second side abuts the base plate; a plurality of bond pads formed on the first side of the supporting structure; and a plurality of conductive bumps formed on the second side of the supporting structure. The plurality of conductive bumps are in contact with the plurality of conductive cups formed on the base plate, and electrically connect the plurality of conductive cups with the plurality of bond pads through conductive feedthroughs in the supporting structure. The thin-film adapter further comprises a cable comprising a plurality of conductive traces in electrical connection with the plurality of bond pads. Each conductive cup of the plurality of conductive cups is in electrical connection with a trace of the plurality of conductive traces via a bond pad of the plurality of bond pads.

In some embodiments, the supporting structure is comprised of one or more layers of dielectric material, and the dielectric material is polyimide, liquid crystal polymer, parylene, polyether ether ketone, or a combination thereof. In some embodiments, the plurality of conductive traces are comprised of one or more layers of conductive material, and the conductive material is platinum (Pt), platinum/iridium (Pt/Ir), titanium (Ti), gold/titanium (Au/Ti), or any alloy thereof. In some embodiments, the plurality of bond pads are comprised of one or more layers of conductive material, and the conductive material is gold (Au), platinum (Pt), platinum/iridium (Pt/Ir), titanium (Ti), gold/titanium (Au/Ti), or any alloy thereof.

In some embodiments, the cable extends from the cavity to an environment exterior of the button. In some embodiments, the supporting structure and the cable are monolithic. In other embodiments, the supporting structure and the cable are separate structures.

In some embodiments, the cylindrical tube comprises: (i) the one or more layers of dielectric material, where the first layer of dielectric material defines an outer diameter of the cylindrical tube and the second layer of dielectric material defines an inner diameter of the tube; and (ii) a core that at least partially fills an interior of the cylindrical tube defined by the inner diameter.

In some embodiments, the plurality of conductive traces are electrically connected with the plurality of bond pads via an anisotropic conductive film or anisotropic conductive paste. In some embodiments, a bond formed between each trace of the plurality of conductive traces and each bond pad of the plurality of bond pads is encapsulated in an insulator. Optionally, the insulator is silicone.

In some embodiments, the button further comprises a flange positioned over the supporting structure and the base plate on the distal end of the housing, where the flange holds the supporting structure abutted against the base plate. In some embodiments, the adapter is removable from the button.

In various embodiments, a thin-film lead assembly is provided comprising: a cable comprising a proximal end, a distal end, a first supporting structure that extends from the proximal end to the distal end, and a first set of conductive traces formed on a portion of the first supporting structure; an electrode assembly formed on the first supporting structure at the distal end of the cable, where the electrode assembly comprises one or more electrodes in electrical connection with one or more conductive traces of the first set of conductive traces; and a connector comprising: (i) a button comprising a base plate and a plurality of conductive connectors on the base plate, and (ii) an adapter comprising a second supporting structure, a plurality of bond pads exposed on a surface of the second supporting structure and electrically connected to the plurality of conductive connectors, and a second set of conductive traces that terminate at the plurality of bond pads. Each trace from the second set of conductive traces terminates at a bond pad of the plurality of bond pads, and the second set of conductive traces of the adapter are in electrical contact with the first set of conductive traces.

In various embodiments, a data acquisition system is provided comprising: a measurement and control device comprising an electronics module; a cable comprising a proximal end, a distal end, a first supporting structure that extends from the proximal end to the distal end, and a first set of conductive traces formed on a portion of the first supporting structure; an electrode assembly formed on the first supporting structure at the distal end of the cable, where the electrode assembly comprises one or more electrodes in electrical connection with one or more conductive traces of the first set of conductive traces; and a connector comprising: (i) a button comprising a base plate and a plurality of conductive connectors on the base plate, and (ii) an adapter comprising a second supporting structure, a plurality of bond pads exposed on a surface of the second supporting structure and electrically connected to the plurality of conductive connectors, and a second set of conductive traces that terminate at the plurality of bond pads. Each trace from the second set of conductive traces terminates at a bond pad of the plurality of bond pads, the second set of conductive traces of the adapter are in electrical contact with the first set of conductive traces, and the connector electrically connects the first set of conductive traces to the electronics module.

BRIEF DESCRIPTION OF THE DRAWINGS

The present invention will be better understood in view of the following non-limiting figures, in which:

FIGS. 2A-2H show a connector in accordance with various embodiments;

DETAILED DESCRIPTION

I. Introduction

Figure 1:
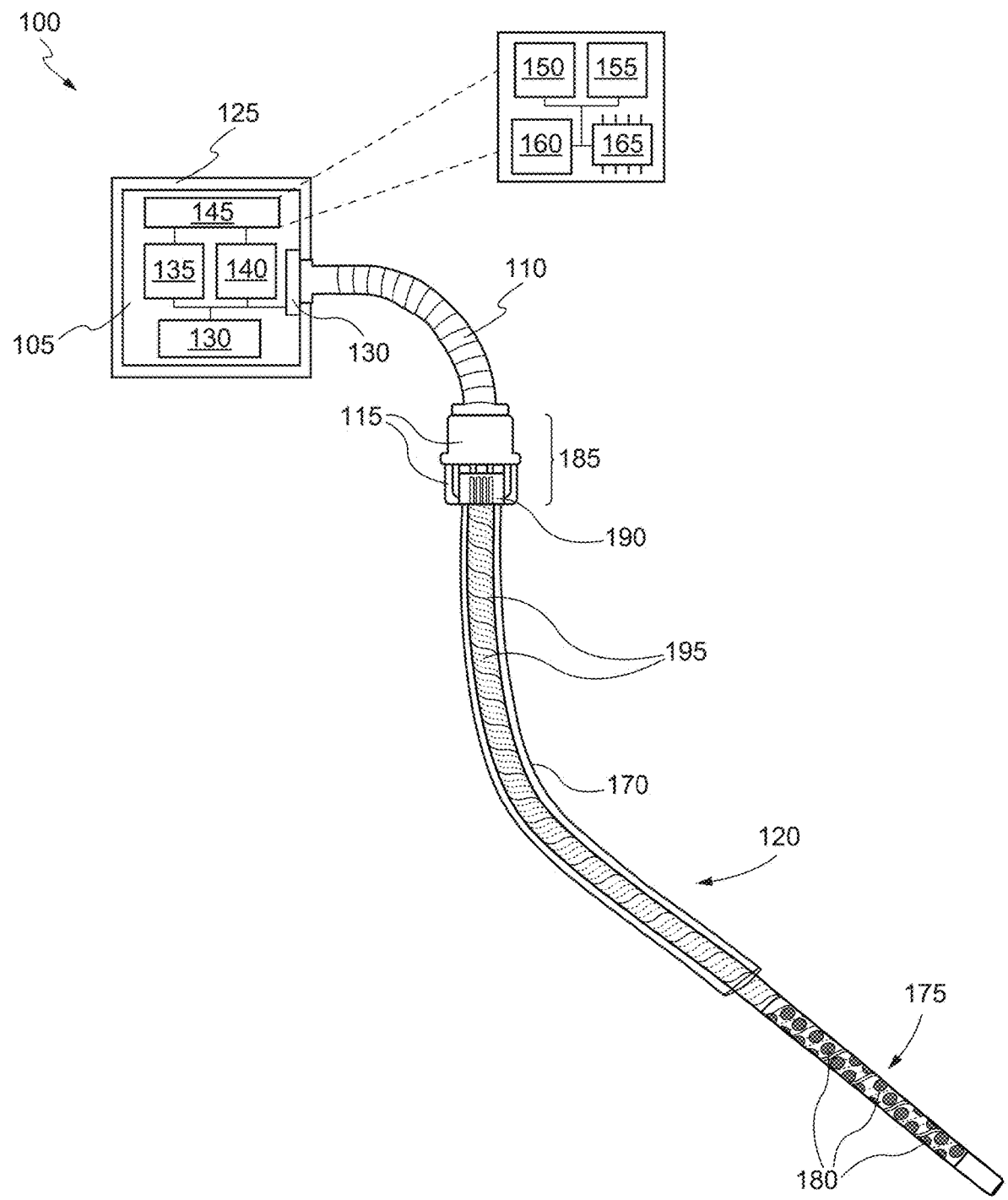
FIG. 1 shows a DAQ system in accordance with various embodiments.

The following disclosure describes proximal connectors compatible with standard DAQ connectors (e.g., head caps with skin buttons) for high density interfaces (e.g., neural interfaces) and methods of microfabricating the proximal connectors. As used herein, the term "proximal" or "proximal end" refers to a first end of the main body, while the term "distal" or "distal end" refers to a second end opposing the first end. For example, the proximal end may be an end of the main body, which is closest to the user, and the distal end may be an end of the main body, which is furthest from the user. The proximal connector may be fabricated using microfabricating techniques. In certain embodiments, the connector is fabricated as a monolithic structure. As used herein, the phrase "monolithic" refers to a device fabricated using a same layer of base material.

As used herein, the phrase "microfabrication" refers to the process of fabricating miniature structures on micrometer scales and smaller. The major concepts and principles of microfabrication are microlithography, doping, thin films, etching, bonding, and polishing. As used herein, the phrase "thin films" refers to a layer of material ranging from fractions of a nanometer (monolayer) to several micrometers in thickness (e.g., between a few nanometers to about 100 µm). Thin films may be deposited by applying a very thin film of material (e.g., between a few nanometers to about 100 urn) onto a substrate surface to be coated, or onto a previously deposited layer of thin film. In various embodiments, a thin film connector is provided comprising a base polymer body (e.g., a supporting structure) and at least one conductive trace formed on the base polymer body. As used herein, the term "high density interface(s)" refers to a interface that comprises at least sixteen electrodes (i.e., recording, sensing, stimulating, other types of electrodes, or combinations thereof). Although the connectors described herein include twelve pins as an example (which is a classic research tool used for preclinical studies), it should be understood that this concept is easily scalable for higher density channel counts (e.g., >100) by using a customized connector with more pins and adjusting the design of the connector in accordance with various aspects disclosed herein.

DAQ systems that include intracranial electrodes placed in brain tissue, neural electrodes placed at extra axial locations, and deep brain electrodes placed in the thalamus electrically interface with neural tissue and record various neurological conditions (e.g., pressure, blood flow, neural activity, brain activity, etc.) through electrical monitoring such as electroencephalography (EEG). As described herein, conventional DAQ systems comprise electronics and a lead assembly containing between four and sixteen sensors or electrodes. There is a need for high-density lead assemblies that can significantly increase the number of sensors or electrodes in order to interface with larger tissue volume, to recruit smaller populations of neurons for recording. Microfabricated thin film neural interfaces have been proposed to significantly increase the number of sensors or electrodes. However, a challenge for microfabricated thin film neural interfaces and thin film lead technology is how to electrically connect the lead assembly to the electronics (which may be positioned outside of the subject's body).

To address these limitations and problems, proximal connectors of various embodiments disclosed herein enable connections with high density neural interfaces and are compatible with standard DAQ connectors such as head caps and skin buttons. One illustrative embodiment of the present disclosure is directed to a connector comprising a flexible adapter that is built monolithically with thin film lead body on the same polymer substrate. In some embodiments, the connector comprises: a button comprising: a housing comprising: a proximal end, a distal end, a cavity, and a base plate positioned in the cavity separating the proximal end and the distal end; and conductive pins extending from the proximal end of the housing through the base plate, and extending into a portion of the cavity on the distal end of the housing. The connector further comprises a thin-film adapter comprising: a supporting structure comprising a main body and a cable. The main body is positioned within the portion of the cavity on the distal end of the housing. The thin-film adapter further comprises bond pads formed on the main body, and a conductive traces formed on the cable and extending onto the main body. The conductive traces terminate at the bond pads. The thin-film adapter further comprises feedthroughs that pass through the bond pads and the main body. Each conductive pin extends through a feedthrough, and each conductive pin is in electrical connection with one or more conductive traces via a bond pad.

In other embodiments, a connector is provided that comprises: a button comprising: a housing comprising: a proximal end, a distal end, a cavity, and a base plate positioned in the cavity separating the proximal end and the distal end; and conductive pins extending from the proximal end of the housing through the base plate, and extending into a portion of the cavity on the distal end of the housing. The connector further comprises a thin-film adapter comprising: a supporting structure positioned within the portion of the cavity on the distal end of the housing; bond pads formed on the supporting structure; a conductive feedthroughs that pass through the supporting structure and are electrically connected to the bond pads; and a cable comprising conductive traces that are electrically connected with the bond pads. Each conductive pin extends through a conductive feedthrough, and each conductive pin is in electrical connection with a conductive trace via a bond pad.

In other embodiments, a connector is provided that comprises: a button comprising: a housing comprising a proximal end, a distal end, and a base plate formed at the distal end; and conductive cups formed on the base plate. The button further comprises: a thin-film adapter comprising: a supporting structure comprising a first side and a second side, where the second side abuts the base plate; bond pads formed on the first side of the supporting structure; and conductive bumps formed on the second side of the supporting structure. The conductive bumps are in contact with the conductive cups formed on the base plate, and electrically connect the conductive cups with the bond pads through conductive feedthroughs in the supporting structure. The thin-film adapter further comprises a cable comprising conductive traces in electrical connection with the bond pads. Each conductive cup is in electrical connection with a conductive trace of via a bond pad.

Advantageously, these approaches provide a connector, which has increased contact points, a smaller footprint, and greater design flexibility. More specifically, these approaches enable connectors with reliable, non-permanent connections between a lead assembly and a DAQ system. This solution is scalable to connecting many electrodes (e.g., greater than sixteen) using a multi flex chip, and thus enabling several monitoring and therapeutic opportunities. Furthermore even for applications where multiple electrodes are not required, various embodiments can be miniaturized to make the system minimally invasive, additionally may make invasive anatomies to become accessible (or navigable) due to the miniaturization. It should be understood that although data acquisition applications are provided as examples of some embodiments, this solution is applicable to all leads and devices that need electrodes/sensors that need to be attached to an electronic device or controller, e.g., a neurostimulator.

II. Data Acquisition Devices and Systems with a Lead Assembly

FIG. 1 shows a data acquisition (DAQ) system 100 in accordance with some aspects of the present invention. In various embodiments, the DAQ system 100 includes a computing device 105, a cable 110, a skin button connector 115, and a lead assembly 120. The computing device 105 (e.g., a data logger or a pulse generator (IPG)) may include a housing 125, a connector 130, a power source 135, a communications device 140 (e.g., a WiFi antenna), and an electronics module 145 (i.e., hardware, software or a combination thereof). The housing 125 may be comprised of materials that are biocompatible such as bioceramics or bioglasses for radio frequency transparency, or metals such as titanium. In accordance with some aspects of the present invention, the size and shape of the housing 125 may be selected such that the computing device 105 can be attached to the exterior of a subject. In the example shown in FIG. 1, the connector 130 is attached to a hole in a surface of the housing 125 such that the housing 125 may be sealed. The connector 130 may include one or more contacts (i.e., electrically conductive elements, pins, wires, tabs, pads, etc.) mounted within the housing 125 or a cap extending from an interior to an exterior of the housing 125. The power source 135 may be within the housing 125 and connected (e.g., electrically connected) to the electronics module 145 to power and operate the components of the electronics module 145. The communications device 140 may be connected (e.g., electrically connected) to the electronics module 145 for wired or wireless communication with external devices via, for example, radiofrequency (RF) telemetry.

In some embodiments, the electronics module 145 may be connected (e.g., electrically connected) to interior ends of the connector 130 such that the electronics module 145 is able to sample or apply a signal or electrical current via conductive traces of the lead assembly 120 connected to the skin button connector 115. As used herein, "conductive" refers to a material's or component's ability to conduct an electric current or electric signal. The electronics module 145 may include discrete and/or integrated electronic circuit components that implement analog and/or digital circuits capable of producing the functions attributed to the data acquisition devices or systems such as sampling signals that measure real world physical conditions and converting the resulting samples into digital numeric values that can be manipulated by a computer. In various embodiments, the electronics module 145 may include software and/or electronic circuit components such as signal conditioning circuitry 150 that converts sensor signals into a form that can be converted to digital values, a controller 155 that determines or senses electrical activity and physiological responses via the electrodes and sensors, an optional 160 analog-to-digital converters to convert conditioned sensor signals to digital values, and a memory 165 with program instructions operable on by the controller 155 to perform one or more processes for sampling or recording signals. In some embodiments, one or more data acquisition applications stored in memory 165 are controlled via controller 155 using software programs, which may be developed by various general purpose programming languages such as Assembly, BASIC, C, C++, C#, Fortran, Java, LabVIEW, Lisp, Pascal, etc.

In various embodiments, the wiring assembly 110 is an assembly of electrical cables, wires, or thin-film conductive traces, which sample signals, transmit signals, transmit electrical power, or a combination thereof, between computing device 105 and lead assembly 120 via the skin button connector 115. The skin button connector 115 is a male connector comprising conductive pins and a cap or a female connector comprising conductive cups and a cap. In some embodiments, the skin button connector 115 is attached to a subject such that the lead assembly may be implanted within the subject while maintaining electrical connection with the wiring assembly 110 and computing device 105, which may be position outside of the subject. For example, the skin button connector 115 may traverse the skin and/or bone layer of a subject. In some embodiments, the skin button connector 115 is configured as a temporary connector such that the wiring assembly 110 and/or lead assembly 120 may be removably plugged into and detached from the skin button connector. A used herein, "electrically connected", "electrical connection", "electrical coupling", "electrical contact", and the like, mean that the two or more components are connected in a manner to complete a circuit affecting electrical current or signal transmission.

In various embodiments, the lead assembly 120 includes a cable or lead body 170, one or more electrode assemblies 175 having one or more electrodes 180 (e.g., one or more sensors), and a connector 185. In some embodiments, the lead assembly 120 is a monolithic structure. In various embodiments, the connector 185 includes skin button connector 115 and a thin-film adapter 190 comprising: (i) a supporting structure, (ii) a plurality of bond pads, (iii) a plurality of conductive traces terminating at the plurality of bond pads, and (iv) a plurality of feedthroughs or vias connecting the plurality of bond pads to the conductive pins or cups of the skin button connector 115. The cable 170 may include one or more conductive traces 195 formed on a supporting structure. In some embodiments, the supporting structure of the cable 170 is the same supporting structure of the adapter 190, and thus the components are monolithic. In other embodiments, the supporting structure of the cable 170 is different from the supporting structure of the adapter 190.

The one or more conductive traces 195 of the cable 170 allow for electrical coupling of the computing device 105 to the electrodes and/or sensors 180 of the electrode assemblies 175 via the connector 185. In some embodiments, the one or more of conductive traces 195 of the cable 170 are the same conductive traces as the plurality of conductive traces of the connector 185 (monolithic traces). In other embodiments, the one or more of conductive traces 195 of the cable 170 are different conductive traces from the plurality of conductive traces of the connector 185 (a different structure but electrically connected). As described herein in detail, the supporting structure may be formed with a dielectric material such as a polymer having suitable dielectric, flexibility and biocompatibility characteristics. Polyurethane, polycarbonate, silicone, polyethylene, fluoropolymer and/or other medical polymers, copolymers and combinations or blends may be used. The conductive material for the traces may be any suitable conductor such as stainless steel, silver, copper or other conductive materials, which may have separate coatings or sheathing for anticorrosive, insulative and/or protective reasons.

The electrode assemblies 175 may include the electrodes and/or sensors 180 fabricated using various shapes and patterns to create certain types of electrode assemblies (e.g., book electrodes, split cuff electrodes, spiral cuff electrodes, epidural electrodes, helical electrodes, probe electrodes, linear electrodes, neural probe, paddle electrodes, intraneural electrodes, etc.). In various embodiments, the electrode assemblies 175 include a base material that provides support for microelectronic structures including the electrodes 180, a wiring layer, optional contacts, etc. In some embodiments, the base material is the supporting structure. The wiring layer may be embedded within or located on a surface of the supporting structure. The wiring layer may be used to electrically connect the electrodes 180 with the one or more conductive traces directly or indirectly via a lead conductor. The term "directly", as used herein, may be defined as being without something in between. The term "indirectly", as used herein, may be defined as having something in between. In some embodiments, the electrodes 195 may make electrical contact with the wiring layer by using the contacts.

III. Thin-Film Connectors and Fabrication Thereof

Figure 2D:
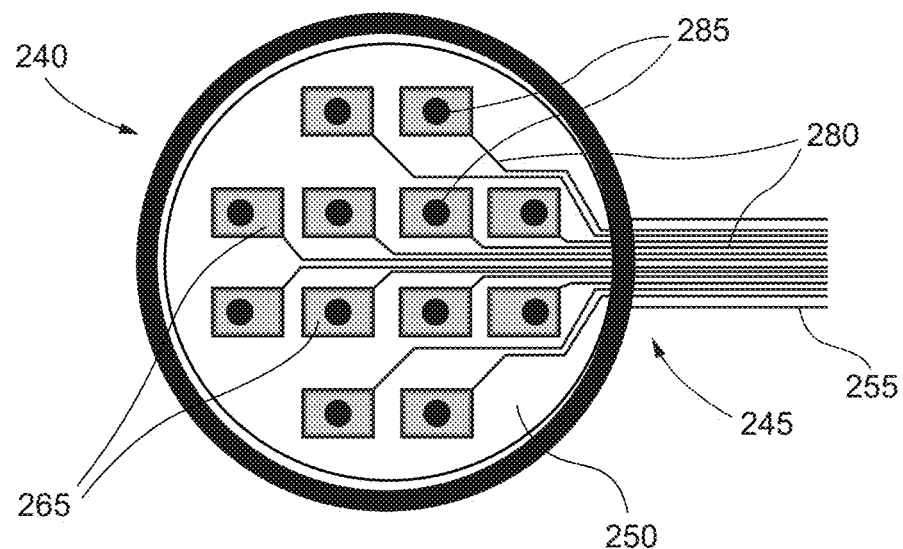
Figure 2E:
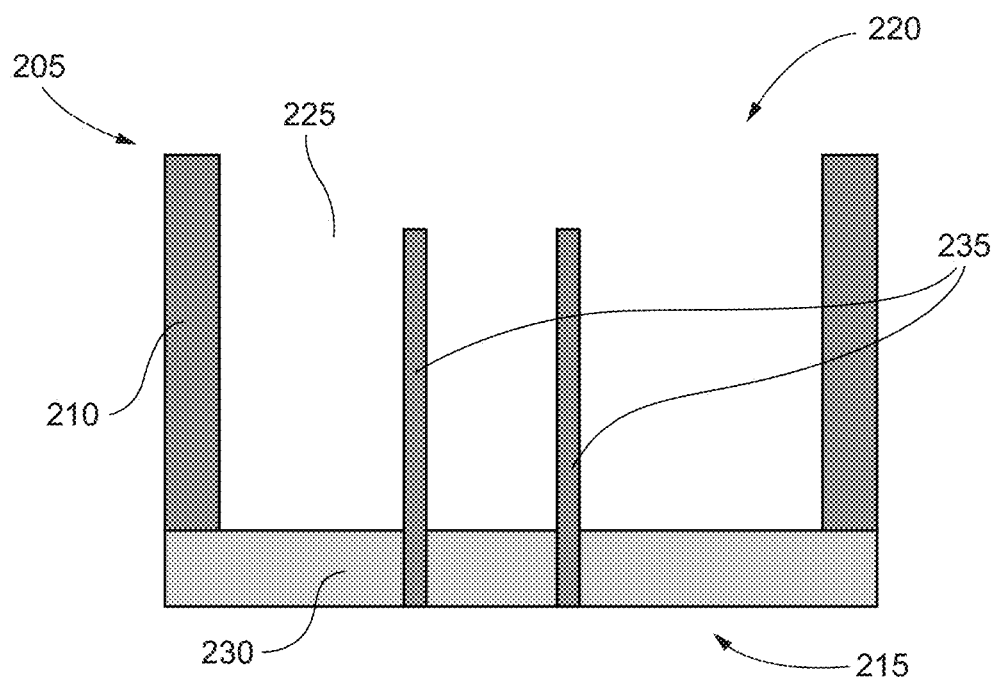

FIGS. 2A-2H show a thin-film connector 200 (e.g., the connector 185 described with respect to FIG. 1) in accordance with aspects of the present disclosure. In various embodiments, the thin-film connector 200 comprises a button 205 comprising a housing 210 having a proximal end 215, a distal end 220, a cavity 225, and a base plate 230 position in the cavity 225 separating the proximal end 215 and the distal end 220. As shown in FIGS. 2A and 2E, the button 205 may be a male button (i.e., presence of conductor pins) with a first portion (a) configured to attach with a second portion (b) that has structure(s) such as a flange for attaching the button 205 to a subject (e.g., a patient). The housing 210 may be comprised of materials that are biocompatible such as bioceramics or bioglasses, or metals such as copper, gold, titanium. In accordance with some aspects, the size and shape of the housing 210 may be selected such that a wiring may traverse via the connector from the exterior of a subject through a layer such as a skin or bone layer into the interior of the subject. In some embodiments, the button 205 further comprises a plurality of conductive pins 235 extending from the proximal end 215 of the housing 210 through the base plate 230, and extending into a portion of the cavity 225 on the distal end 220 of the housing 210. The base plate 230 may be made of an insulator such as a polymer or dielectric material.

Figure 2F:
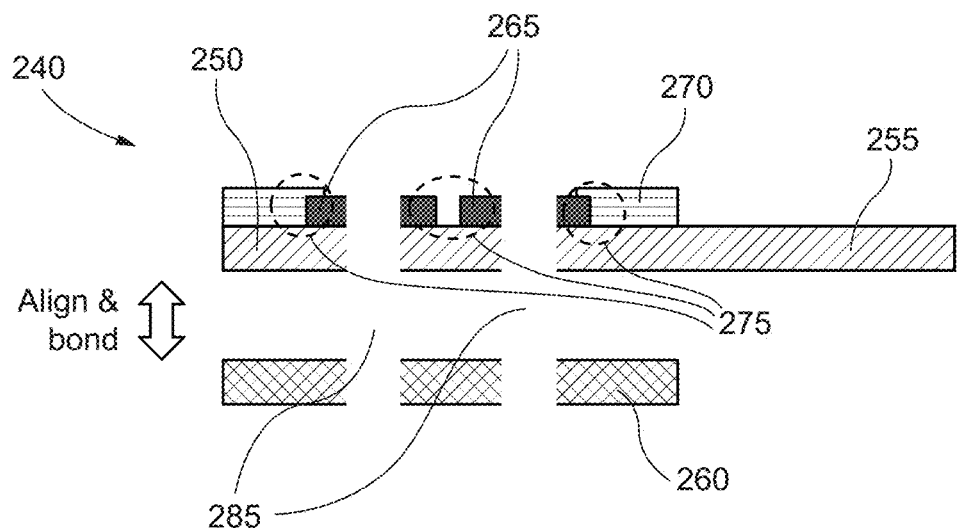
Figure 2G:
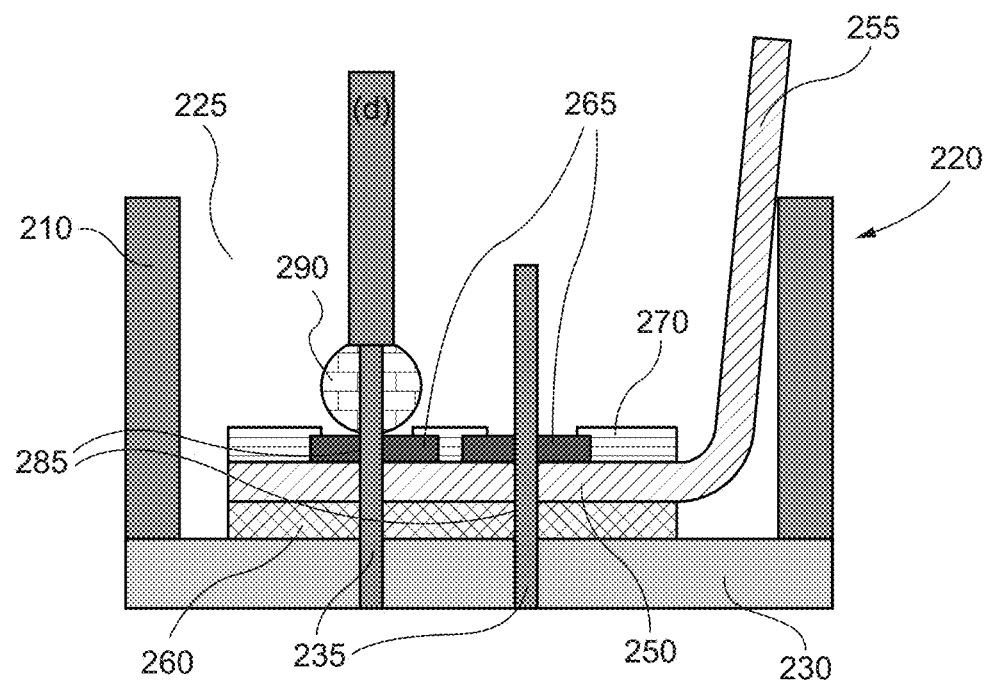
Figure 2H:
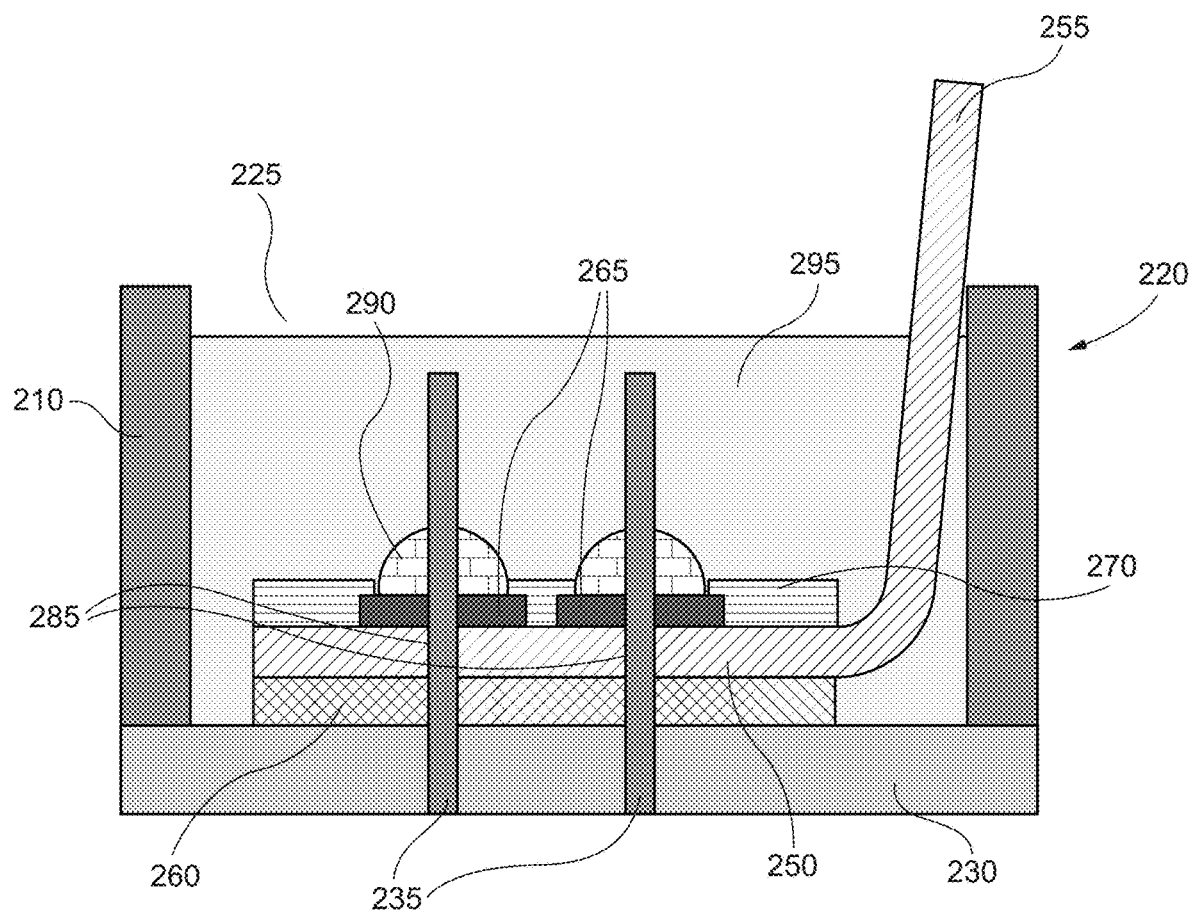

As shown in FIGS. 2D and 2F, the thin-film connector 200 may further comprise a thin-film adapter 240. In various embodiments, the thin-film adapter 240 comprises a supporting structure 245 comprising a main body 250 and a cable 255. In some embodiments, the thin-film adapter 240 is built monolithically with the thin-film lead body (e.g., the lead body 170 discussed with respect to FIG. 1) on a same polymer substrate, e.g., supporting structure 245. The supporting structure 245 may be comprised of one or more layers of dielectric material. In some embodiments, the dielectric material is a polymer such as a polymer of imide monomers (i.e., a polyimide), a liquid crystal polymer (LCP) such as Kevlar®, parylene, polyether ether ketone (PEEK), or combinations thereof. In certain embodiments, the dielectric material is polyimide, LCP, parylene, PEEK, or a combination thereof. As shown in FIGS. 2B, 2C, 2G, and 2H, the main body 250 may be positioned within the portion of the cavity 225 on the distal end 220 of the housing 210. As shown in FIG. 2D, the main body 250 may be patterned into a particular shape such as a circle to fit inside of the cavity 225 of the button 205. During assembling as shown in FIGS. 2B and 2C, the main body 250 may be pushed into the cavity 225 of the skin button 205. In some embodiments, the cable 255 extends from the cavity 225 to an environment exterior of the button 205 (e.g., an environment inside a subject or outside of a subject). In some embodiments, the main body 250 of the supporting structure 245 and the cable 255 of the supporting structure 245 are monolithic. As shown in FIGS. 2F-2H, the thin-film adapter 240 may further comprises pressure sensitive adhesive 260 that attaches the main body 250 to the base plate 230 when the main body 250 is pushed into the cavity 225 of the skin button 205. As such, in certain embodiments, the thin-film adapter 240 is not removable from the button 205 once assembled.

As shown in FIGS. 2D and 2F-2H, the thin-film adapter 240 may further comprise a plurality of bond pads 265 formed on the main body 250. In some embodiments, the bond pads 265 are comprised of one or more layers of conductive material. In certain embodiments, the conductive material is gold (Au), platinum (Pt), platinum/iridium (Pt/Ir), titanium (Ti), gold/titanium (Au/Ti), or any alloy thereof. A shown in FIGS. 2F-2H, the thin-film adapter 240 may further comprise an insulation layer 270 formed over the main body 250 of the supporting structure 245 and at least a portion 275 of one or more bond pads of the plurality of bond pads 265. In some embodiments, the insulation layer 270 comprises one or more layers of polymer or dielectric. As shown in FIG. 2D, the thin-film adapter 240 may further comprise a plurality of conductive traces 280 formed on the cable 255 and extending onto the main body 250. In some embodiments, the plurality of conductive traces 280 terminate at the plurality of bond pads 265. In certain embodiments, each trace from the plurality of conductive traces 280 terminates at a bond pad from the plurality of bond pads 265. In other embodiments, one or more traces from the plurality of conductive traces 280 terminate at each bond pad from the plurality of bond pads 265. In other embodiments, each trace from the plurality of conductive traces 280 terminates at a corresponding bond pad from the plurality of bond pads 265 such that there is a one to one relationship between the traces and the bond pads. In some embodiments, the plurality of conductive traces 280 are comprised of one or more layers of conductive material. In certain embodiments, the conductive material is platinum (Pt), platinum/iridium (Pt/Ir), titanium (Ti), gold/titanium (Au/Ti), or any alloy thereof.

As shown in FIGS. 2D and 2F-2H, the thin-film adapter 240 may further comprise a plurality of feedthroughs 285 that pass through the plurality of bond pads 265 and the main body 250. In some embodiments, each conductive pin of the plurality of conductive pins 235 extends through a feedthrough of the plurality of feedthroughs 285, and each conductive pin is in electrical connection with the one or more traces of the plurality of conductive traces 280 via each bond pad of the plurality of bond pads 265. As shown in FIGS. 2G and 2H, a conductive epoxy 290 may be disposed on a bottom of each conductive pin of the plurality of conductive pins 235 and each bond pad of the plurality of bond pads 265, respectively, to electrically connect each conductive pin to a corresponding bond pad. The conductive epoxy 290 may be dispensed using a dispensing needle (d) onto the bottom of each conductive pin to form electrical connection between the conductive pins 235 and the bond pads 265. In some embodiments. A digital dispenser is used to accurately control epoxy droplet's volume to prevent shorts. As shown in FIG. 2H, a backfill layer 295 may be formed over the main body 250 of the supporting structure 245 and fills a majority of a volume of the cavity 225 of the housing 210. For example, after curing the conductive epoxy 290, a non-conductive material such as silicone may be backfilled into a majority of a volume of the cavity 225 in order to reinforce the bonds and work as a strain relief for the cable 255. A used herein, a "majority" is the greater part, or more than half, of the total. For example, a majority may be a subset of the total volume of the cavity 225 after the conductive pins and adapter are disposed in the cavity, and the subset consists of more than half of the total volume.

Figure 3A:
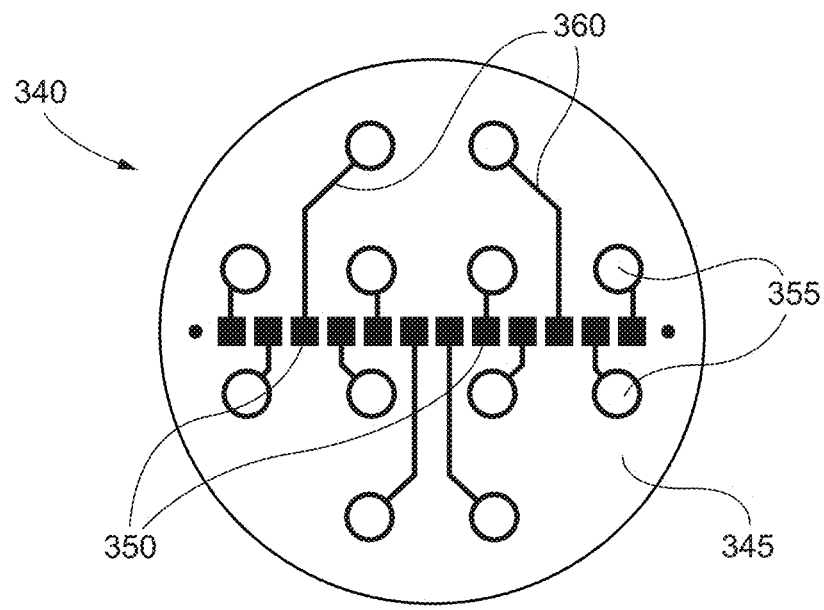
FIGS. 3A-3E show an alternative connector in accordance with various embodiments.
Figure 3B:
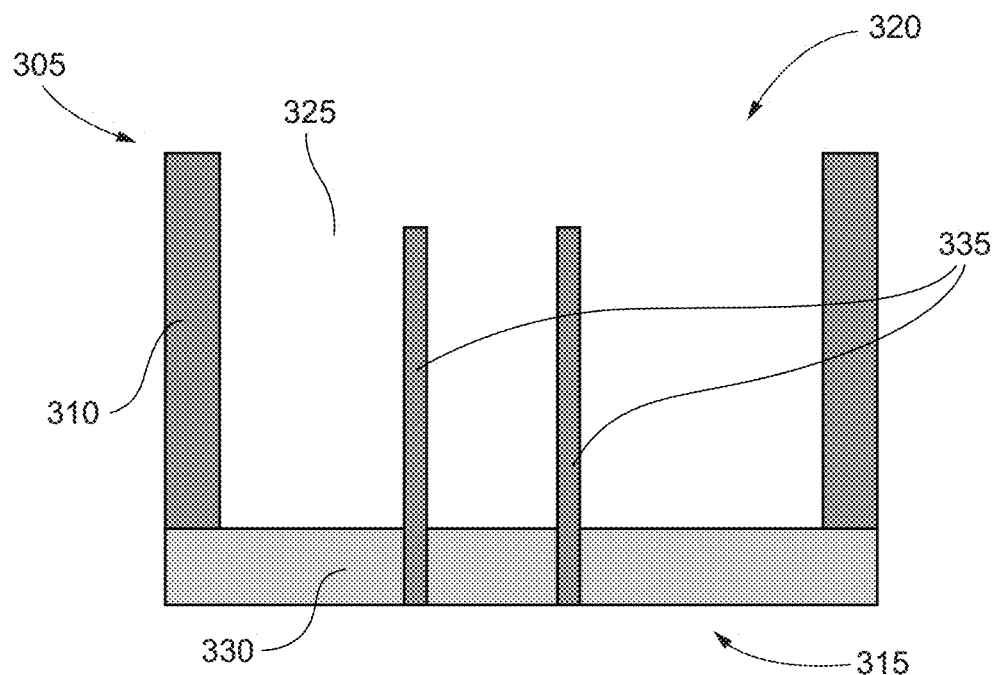

FIGS. 3A-3E show an alternative thin-film connector 300 (e.g., the connector 185 described with respect to FIG. 1) in accordance with aspects of the present disclosure. In various embodiments, the thin-film connector 300 comprises a button 305 comprising a housing 310 having a proximal end 315, a distal end 320, a cavity 325, and a base plate 330 position in the cavity 325 separating the proximal end 315 and the distal end 320. As shown in FIG. 3B (and as described with respect to FIG. 2A), the button 305 may be a male button (i.e., presence of conductor pins) with a first portion (a) configured to attach with a second portion (b) that has structure(s) such as a flange for attaching the button 305 to a subject (e.g., a patient). The housing 310 may be comprised of materials that are biocompatible such as bioceramics or bioglasses, or metals such as copper, gold, titanium. In accordance with some aspects, the size and shape of the housing 310 may be selected such that a wiring may traverse via the connector from the exterior of a subject through a layer such as a skin or bone layer into the interior of the subject. In some embodiments, the button 305 further comprises a plurality of conductive pins 335 extending from the proximal end 315 of the housing 310 through the base plate 330, and extending into a portion of the cavity 325 on the distal end 320 of the housing 310. The base plate 330 may be made of an insulator such as a polymer or dielectric material.

Figure 3C:
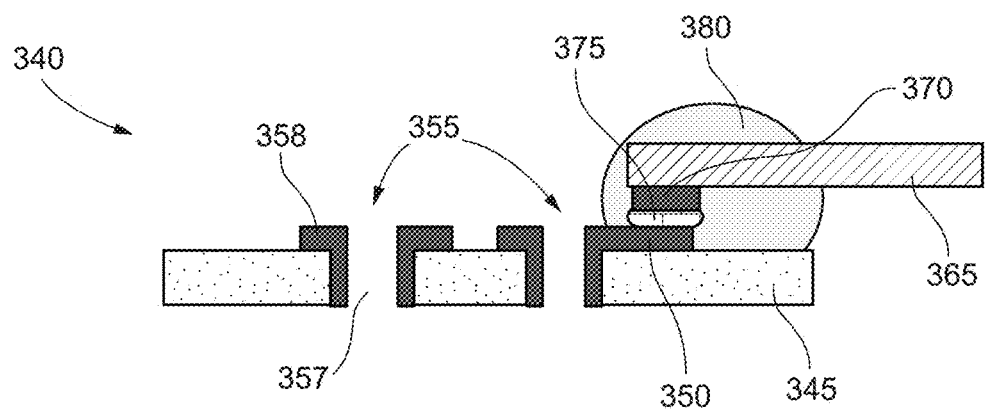
Figure 3D:
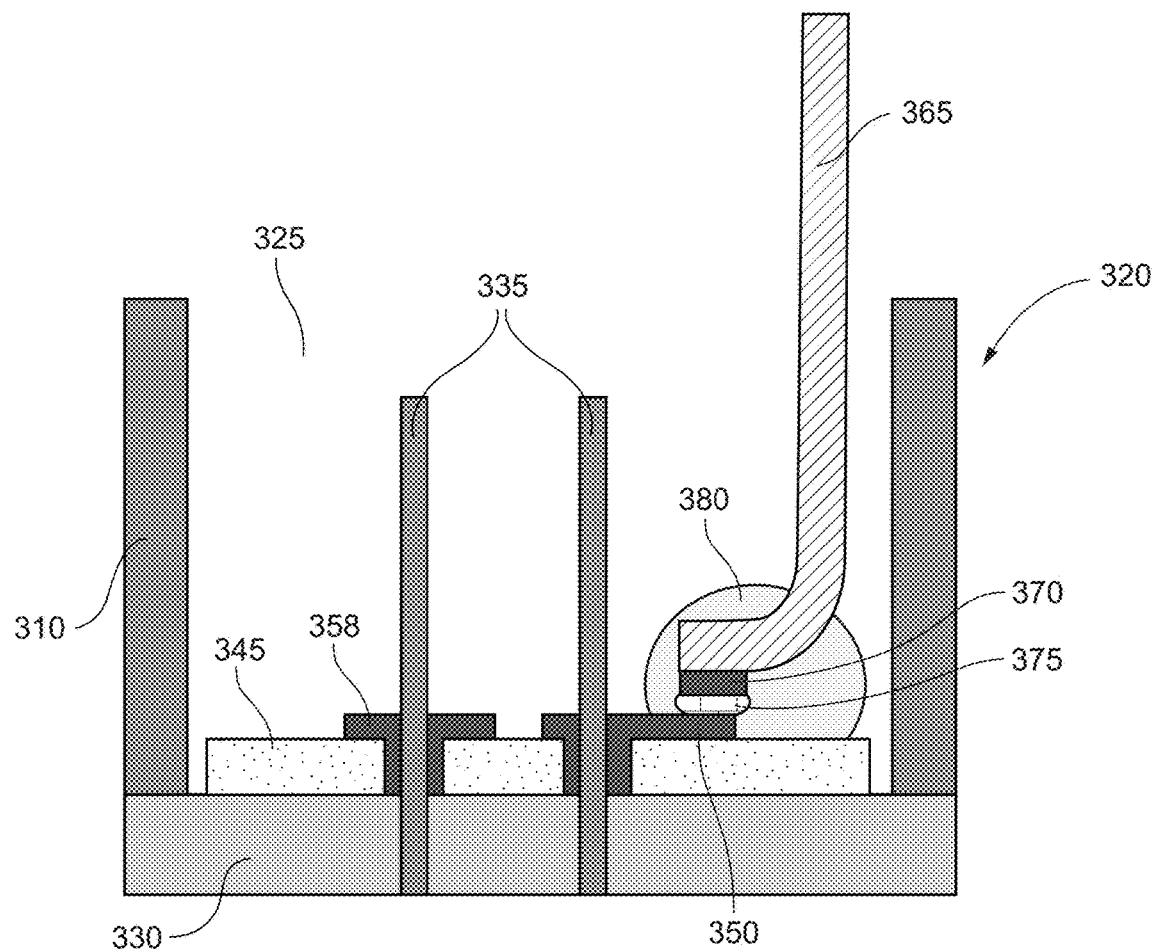
Figure 3E:
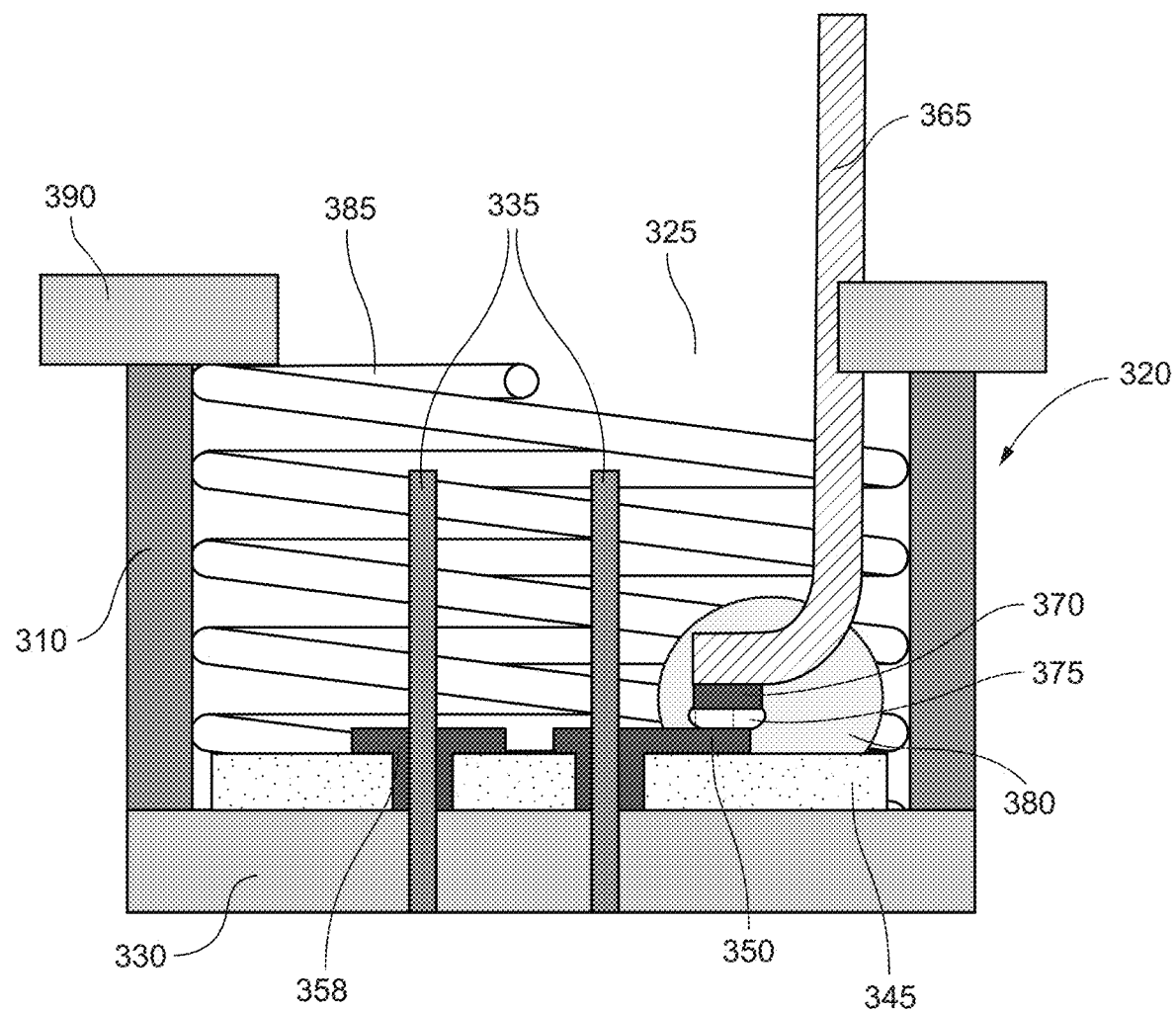

As shown in FIGS. 3A and 3C-3E, the thin-film connector 300 may further comprise a thin-film adapter 340. In various embodiments, the thin-film adapter 340 comprises a supporting structure 345. The supporting structure 345 may be comprised of one or more layers of dielectric material. In some embodiments, the dielectric material is a polymer such as a polymer of imide monomers (i.e., a polyimide), a LCP, parylene, PEEK, or combinations thereof. In certain embodiments, the dielectric material is polyimide, LCP, parylene, PEEK, or a combination thereof. As shown in FIGS. 3D and 3E, the supporting structure 345 may be positioned within the portion of the cavity 325 on the distal end 320 of the housing 310. For example, during assembling as described with respect to FIGS. 2B and 2C, the supporting structure 345 may be pushed into the cavity 325 of the skin button 305. As shown in FIG. 3A, the supporting structure 345 may be patterned into a particular shape such as a circle to fit inside of the cavity 325 of the button 305.

As shown in FIGS. 3A and 3C-3E, the thin-film adapter 340 may further comprise a plurality of bond pads 350 formed on the supporting structure 345. In some embodiments, the bond pads 350 are comprised of one or more layers of conductive material. In certain embodiments, the conductive material is gold (Au), platinum (Pt), platinum/iridium (Pt/Ir), titanium (Ti), gold/titanium (Au/Ti), or any alloy thereof. A shown in FIGS. 3A and 3C-3E, the thin-film adapter 340 may further comprise a plurality of conductive feedthroughs 355 that pass through the supporting structure 345 and are electrically connected to the plurality of bond pads 350. In some embodiments, the conductive feedthroughs 355 are comprised of a via 357 and one or more layers of conductive material 358. The vias 357 may be lined with one or more layers of the conductive material 358. In certain embodiments, the conductive material 358 is gold (Au), platinum (Pt), platinum/iridium (Pt/Ir), titanium (Ti), gold/titanium (Au/Ti), or any alloy thereof. The plurality of conductive feedthroughs 355 may be electrically connected to the plurality of bond pads 350 by direct contact or indirect contact, for example, by way of one or more conductive traces 360.

As shown in FIGS. 3C-3E, the thin-film adapter 340 may further comprise a cable 365 comprising a plurality of conductive traces 370 (see also in FIG. 2D with respect to cable 255 and conductive traces 280) that are electrically connected with the plurality of bond pads 350. The cable 365 may extend from the cavity 325 to an environment exterior of the button 305. In some embodiments, the cable 365 is built monolithically with the thin-film lead body (e.g., the lead body 170 discussed with respect to FIG. 1) on a same polymer substrate, e.g., supporting structure. In some embodiments, the supporting structure 345 and the cable 365 are monolithic, as described with respect to FIGS. 2B-2H. In other embodiments, the supporting structure 345 and the cable 365 are separate structures. As shown in FIGS. 3C-3E, when the supporting structure 345 and the cable 365 are separate structures, the plurality of conductive traces 370 may be electrically connected with the plurality of bond pads 350 via an anisotropic conductive film or anisotropic conductive paste 375. In some embodiments, a bond formed between each trace of the plurality of conductive traces 370 and each bond pad of the plurality of bond pads 350 is encapsulated in an insulator 380. In certain embodiments, the insulator 380 is a polymer such as silicone.

In some embodiments, the plurality of conductive traces 370 terminate at the plurality of bond pads 350. In certain embodiments, each trace from the plurality of conductive traces 370 terminates at a bond pad from the plurality of bond pads 350. In other embodiments, one or more traces from the plurality of conductive traces 370 terminate at each bond pad from the plurality of bond pads 350. In other embodiments, each trace from the plurality of conductive traces 370 terminates at a corresponding bond pad from the plurality of bond pads 350 such that there is a one to one relationship between the traces and the bond pads. In some embodiments, the plurality of conductive traces 370 are comprised of one or more layers of conductive material. In certain embodiments, the conductive material is platinum (Pt), platinum/iridium (Pt/Ir), titanium (Ti), gold/titanium (Au/Ti), or any alloy thereof. As shown in FIGS. 3D and 3E, each conductive pin of the plurality of conductive pins 335 extends through a conductive feedthrough of the plurality of feedthroughs 355, and each conductive pin is in electrical connection with a trace of the plurality of conductive traces 370 via a bond pad of the plurality of bond pads 350.

As shown in FIG. 3E, the button 305 may further comprise a spring 385 positioned over the supporting structure 345 and the base plate 330 within the portion of the cavity 325 on the distal end 320 of the housing 310. In some embodiments, a cap 390 is provided over a portion of the housing 310 that holds the spring 385 under compression within the portion of the cavity 325 on the distal end 320 of the housing. As such, the spring 385 holds the supporting structure 345 abutted against the base plate 330, and the thin-film adapter 340 is removable from the button 305 once assembled (after removal of the cap 390 and spring 385). In some embodiments, an outer diameter of the spring 385 matches an inner diameter of the housing 310. In some embodiments, the spring 385 is positioned in direct contact with the supporting structure 345. In other embodiments, the spring 385 is positioned in indirect contact with the supporting structure 345, for example, an insulator layer may be disposed between the spring 385 and the supporting structure 345.

Figure 4A:
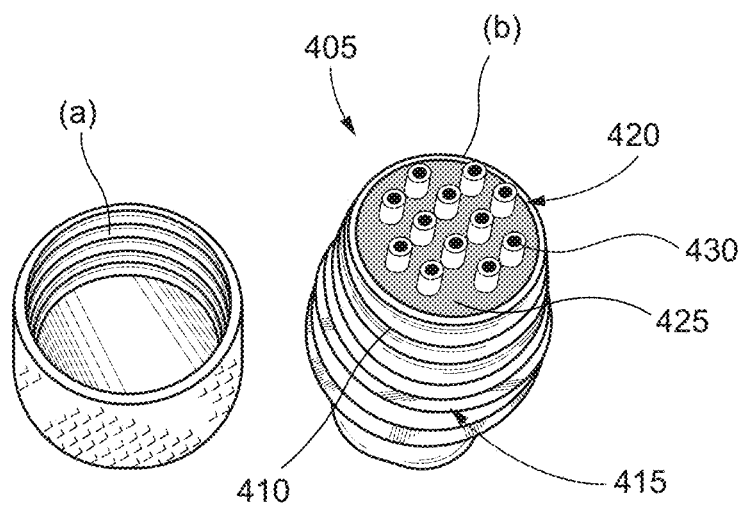
FIGS. 4A-4G show an alternative connector in accordance with various embodiments.
Figure 4B:
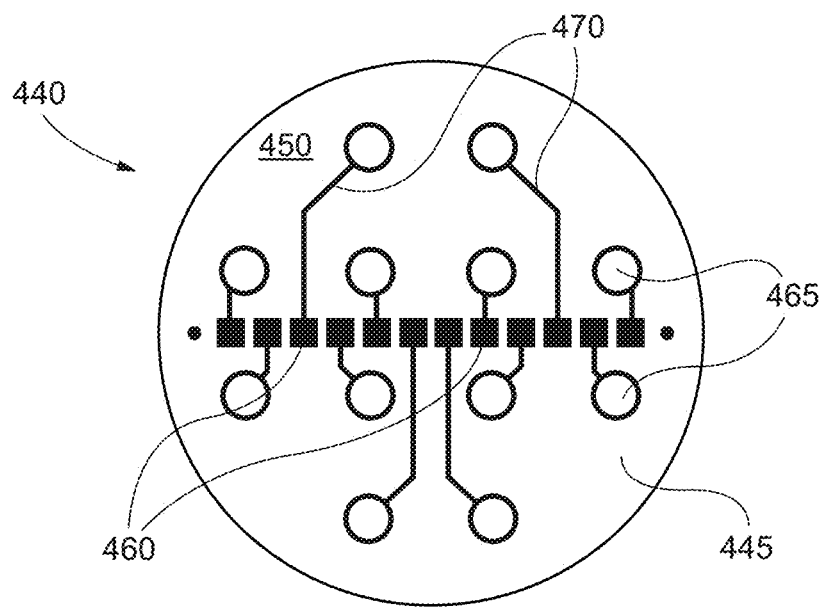
Figure 4C:
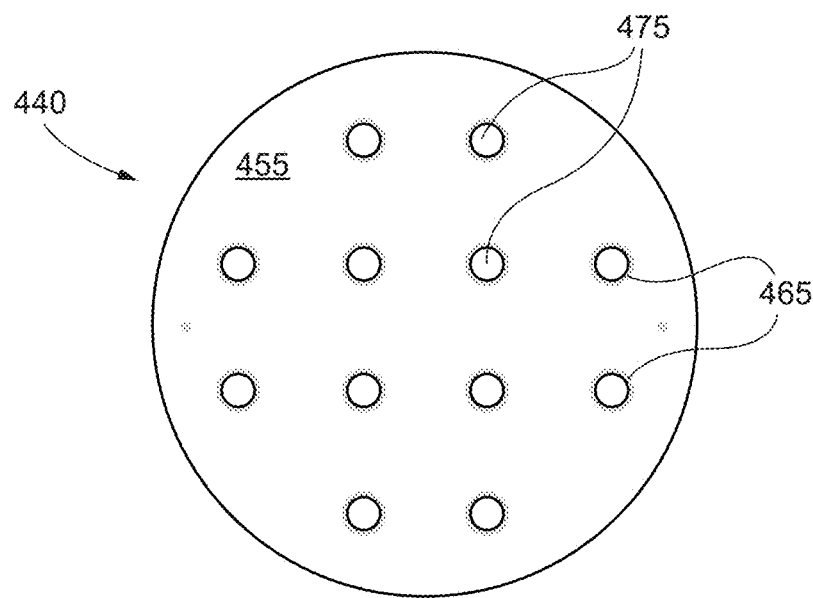
Figure 4D:
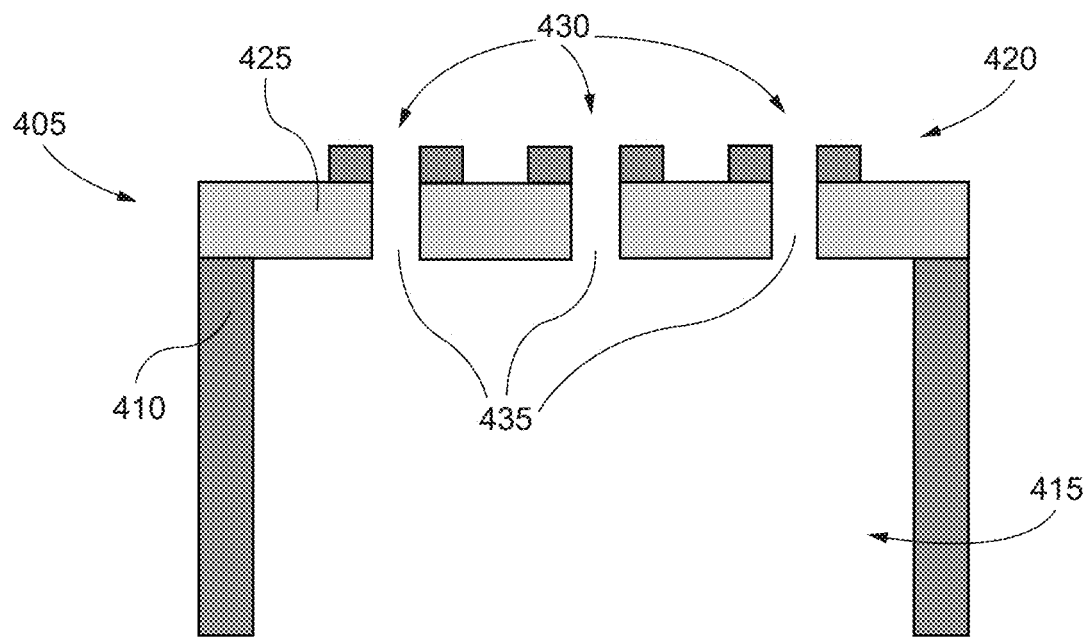

FIGS. 4A-4G show an alternative thin-film connector 400 (e.g., the connector 185 described with respect to FIG. 1) in accordance with aspects of the present disclosure. In various embodiments, the thin-film connector 400 comprises a button 405 comprising a housing 410 having a proximal end 415, a distal end 420, and a base plate 425 formed at the distal end 420. As shown in FIGS. 4A and 4D, the button 405 may be a female button (i.e., presence of conductor cups or solder cups) with a first portion (a) configured to attach with a second portion (b) that has structure(s) such as a flange for attaching the button 405 to a subject (e.g., a patient). The housing 410 may be comprised of materials that are biocompatible such as bioceramics or bioglasses, or metals such as copper, gold, titanium. In accordance with some aspects, the size and shape of the housing 410 may be selected such that a wiring may traverse via the connector from the exterior of a subject through a layer such as a skin or bone layer into the interior of the subject. In some embodiments, the button 405 further comprises a plurality of conductive cups or solder cups 430 formed on the base plate 425. The conductive cups 430 may comprise holes or vias 435 extending from the proximal end 415 of the housing 410 through the base plate 425 to the distal end 420 of the housing 410. The base plate 425 may be made of an insulator such as a polymer or dielectric material.

Figure 4E:
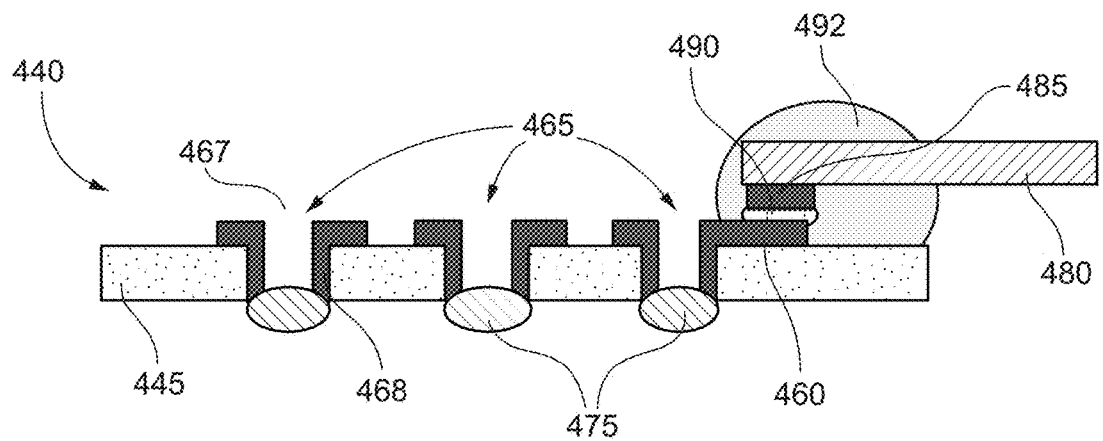
Figure 4F:
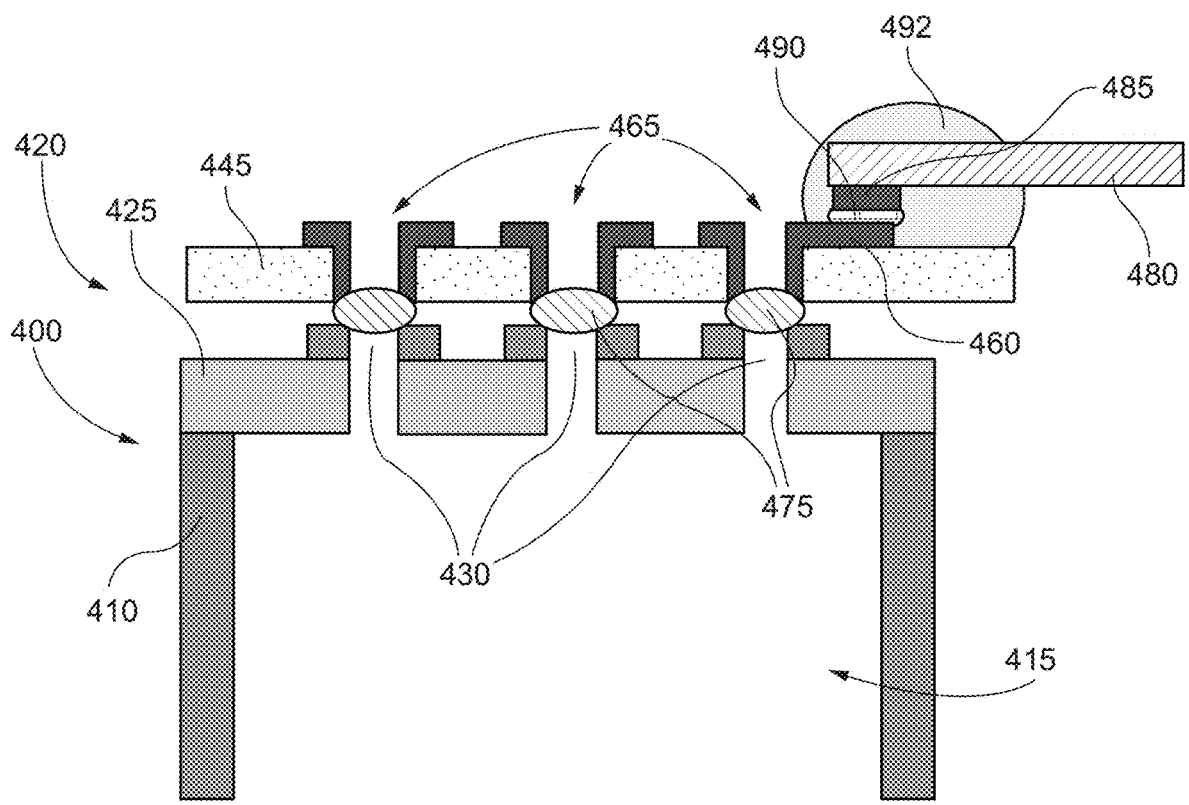
Figure 4G:
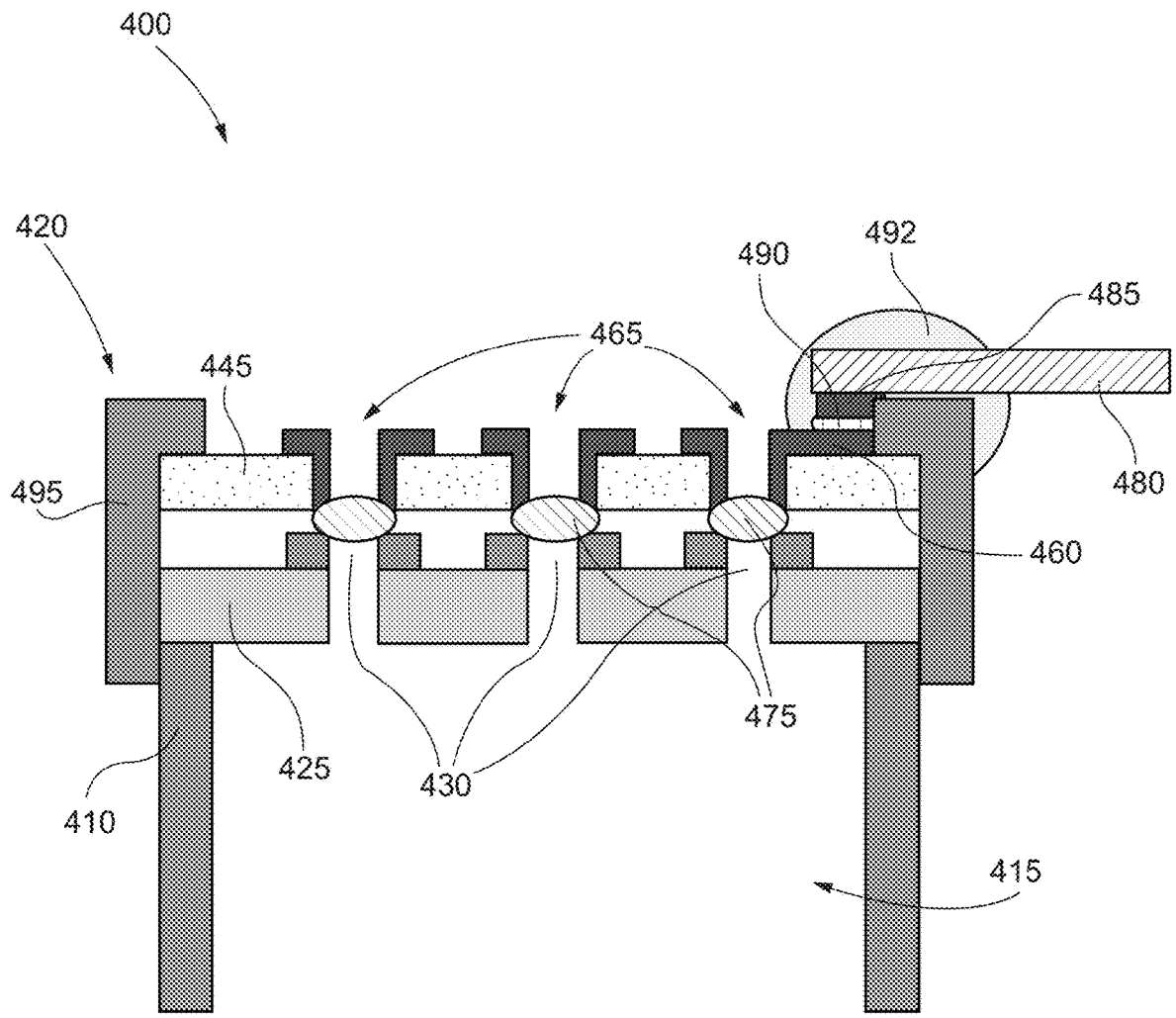

As shown in FIGS. 4B, 4C, and 4E-4G, the thin-film connector 400 may further comprise a thin-film adapter 440. In various embodiments, the thin-film adapter 440 comprises a supporting structure 445. As shown in FIGS. 4B and 4C, the supporting structure 445 may comprise a first side 450 and a second side 455. The supporting structure 445 may be comprised of one or more layers of dielectric material. In some embodiments, the dielectric material is a polymer such as a polymer of imide monomers (i.e., a polyimide), a LCP, parylene, PEEK, or combinations thereof. In certain embodiments, the dielectric material is polyimide, LCP, parylene, PEEK, or a combination thereof. As shown in FIGS. 4F and 4G, the supporting structure 445 may be positioned abutting the base plate 425 on the distal end 420 of the housing 410. For example, during assembling, the supporting structure 445 may be placed abutting the base plate 425 to make contact with the conductive cups 430. As shown in FIGS. 4B and 4C, the supporting structure 445 may be patterned into a particular shape such as a circle to fit on top of the base plate 425 of the button 405.

As shown in FIGS. 4B and 4E-4G, the thin-film adapter 440 may further comprise a plurality of bond pads 460 formed on the supporting structure 445. The plurality of bond pads 460 may be formed on the first side 450 of the supporting structure. In some embodiments, the bond pads 460 are comprised of one or more layers of conductive material. In certain embodiments, the conductive material is gold (Au), platinum (Pt), platinum/iridium (Pt/Ir), titanium (Ti), gold/titanium (Au/Ti), or any alloy thereof. A shown in FIGS. 4B and 4E-4G, the thin-film adapter 440 may further comprise a plurality of conductive feedthroughs 465 that pass through the supporting structure 445 and are electrically connected to the plurality of bond pads 460. In some embodiments, the conductive feedthroughs 465 are comprised of a via 467 and one or more layers of conductive material 468. The vias 467 may be lined with one or more layers of the conductive material 468. In certain embodiments, the conductive material 468 is gold (Au), platinum (Pt), platinum/iridium (Pt/Ir), titanium (Ti), gold/titanium (Au/Ti), or any alloy thereof. The plurality of conductive feedthroughs 465 may be electrically connected to the plurality of bond pads 460 by direct contact or indirect contact, for example, by way of one or more conductive traces 470.

As shown in FIGS. 4C and 4E-4G, the thin-film adapter 440 may further comprise a plurality of conductive bumps 475 formed on the second side 455 of the supporting structure 445. In some embodiments, the plurality of conductive bumps 475 are in contact with the plurality of solder cups 430 formed on the base plate 425, and electrically connect the plurality of solder cups 430 with the plurality of bond pads 460 through conductive feedthroughs 465 in the supporting structure 445. For example, on the second side 455 a conductive paste such as solder paste may be screen printed and then reflowed to form semi-hemispheric conductive bumps 475. The conductive bumps 475 are connected to bond pads 460 on the first side 450 of the supporting structure 445 through the metallized vias 467. In some embodiments, the conductive bumps 475 are comprised of conductive material or solder. In certain embodiments, the conductive material is tin (Sn), lead (Pb), zinc (Zn), cadmium (Cd), silver (Ag), bismuth (Bi), or any alloy thereof.

As shown in FIGS. 4E-4F, the thin-film adapter 440 may further comprise a cable 480 comprising a plurality of conductive traces 485 (see also in FIG. 2D with respect to cable 255 and conductive traces 280) that are electrically connected with the plurality of bond pads 460. The cable 480 may extend from the base plate 425 to an environment exterior of the button 405. In some embodiments, the cable 480 is built monolithically with the thin-film lead body (e.g., the lead body 170 discussed with respect to FIG. 1) on a same polymer substrate, e.g., supporting structure. In some embodiments, the supporting structure 445 and the cable 480 are monolithic, as described with respect to FIGS. 2B-2H. In other embodiments, the supporting structure 445 and the cable 480 are separate structures. As shown in FIGS. 4E-4G, when the supporting structure 445 and the cable 480 are separate structures, the plurality of conductive traces 485 may be electrically connected with the plurality of bond pads 460 via an anisotropic conductive film or anisotropic conductive paste 490. In some embodiments, a bond formed between each trace of the plurality of conductive traces 485 and each bond pad of the plurality of bond pads 460 is encapsulated in an insulator 492. In certain embodiments, the insulator 492 is a polymer such as silicone.

In some embodiments, the plurality of conductive traces 485 terminate at the plurality of bond pads 460. In certain embodiments, each trace from the plurality of conductive traces 485 terminates at a bond pad from the plurality of bond pads 460. In other embodiments, one or more traces from the plurality of conductive traces 485 terminate at each bond pad from the plurality of bond pads 460. In other embodiments, each trace from the plurality of conductive traces 485 terminates at a corresponding bond pad from the plurality of bond pads 460 such that there is a one to one relationship between the traces and the bond pads. In some embodiments, the plurality of conductive traces 485 are comprised of one or more layers of conductive material. In certain embodiments, the conductive material is platinum (Pt), platinum/iridium (Pt/Ir), titanium (Ti), gold/titanium (Au/Ti), or any alloy thereof. As shown in FIGS. 4F and 4G, each conductive cup of the plurality of conductive cups 430 is in electrical connection with a trace of the plurality of conductive traces 485 via a bond pad of the plurality of bond pads 460.

As shown in FIG. 4G, the button 405 may further comprise cap having a flange 495 positioned over the supporting structure 445 and the base plate 425 on the distal end 420 of the housing 410. As such, the flange 495 holds the supporting structure 445 abutted against the base plate 425, and the thin-film adapter 440 is removable from the button 405 once assembled (after removal of the cap and flange 495). In some embodiments, the flange 495 is positioned in direct contact with the supporting structure 445. In other embodiments, the flange 495 is positioned in indirect contact with the supporting structure 445, for example, an insulator layer may be disposed between the flange 495 and the supporting structure 445.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A thin-film lead assembly comprising:
    a cable comprising a proximal end, a distal end, a first supporting structure that extends from the proximal end to the distal end, and a first set of conductive traces formed on a portion of the first supporting structure;
    an electrode assembly formed on the first supporting structure at the distal end of the cable, wherein the electrode assembly comprises one or more electrodes in electrical connection with one or more conductive traces of the first set of conductive traces; and
    a connector comprising: (i) a button comprising a base plate and a plurality of conductive connectors on the base plate, and (ii) an adapter comprising a second supporting structure, a plurality of bond bands exposed on a surface of the second supporting structure and electrically connected to the plurality of conductive connectors, and a second set of conductive traces that terminate at the plurality of bond bands,
    wherein each trace from the second set of conductive traces terminates at a bond pad of the plurality of bond pads, and
    wherein the second set of conductive traces of the adapter are in electrical contact with the first set of conductive traces.

2. The thin-film lead assembly of claim 1, wherein the button further comprises a housing comprising: a proximal end, a distal end, a cavity, and the base plate positioned in the cavity separating the proximal end and the distal end.

3. The thin-film lead assembly of claim 2, wherein the plurality of conductive connectors extend from the proximal end of the housing through the base plate, and extend into a portion of the cavity on the distal end of the housing.

4. The thin-film lead assembly of claim 2, wherein the second supporting structure comprises a main body positioned within the portion of the cavity on the distal end of the housing.

5. The thin-film lead assembly of claim 4, wherein the main body and the cable are monolithic.

6. The thin-film lead assembly of claim 1, wherein the second supporting structure is comprised of one or more layers of dielectric material, and the dielectric material is polyimide, liquid crystal polymer, parylene, polyether ether ketone, or a combination thereof.

7. The thin-film lead assembly of claim 1, wherein the second set of conductive traces are comprised of one or more layers of conductive material, and the conductive material is platinum (Pt), platinum/iridium (Pt/Ir), titanium (Ti), gold/titanium (Au/Ti), or any alloy thereof.

8. The thin-film lead assembly of claim 1, where the plurality of bond pads are comprised of one or more layers of conductive material, and the conductive material is gold (Au), platinum (Pt), platinum/iridium (Pt/Ir), titanium (Ti), gold/titanium (Au/Ti), or any alloy thereof.

9. The thin-film lead assembly of claim 1, wherein the adapter further comprises a conductive epoxy disposed on a bottom of each conductive connector of the plurality of conductive connectors and each bond pad of the plurality of bond pads, respectively, to electrically connect each conductive connector to a corresponding bond pad.

10. The thin-film lead assembly of claim 4, wherein the adapter further comprises an insulation layer formed over the main body of the second supporting structure and at least a portion of each bond pad of the plurality of bond pads.

11. The thin-film lead assembly of claim 4, wherein the adapter further comprises a backfill layer formed over the main body of the second supporting structure and fills a majority of a volume of the cavity of the housing.

12. A data acquisition system comprising:
    a measurement and control device comprising an electronics module;
    a cable comprising a proximal end, a distal end, a first supporting structure that extends from the proximal end to the distal end, and a first set of conductive traces formed on a portion of the first supporting structure;

an electrode assembly formed on the first supporting structure at the distal end of the cable, wherein the electrode assembly comprises one or more electrodes in electrical connection with one or more conductive traces of the first set of conductive traces; and
a connector comprising: (i) a button comprising a base plate and a plurality of conductive connectors on the base plate, and (ii) an adapter comprising a second supporting structure, a plurality of bond bands exposed on a surface of the second supporting structure and electrically connected to the plurality of conductive connectors, and a second set of conductive traces that terminate at the plurality of bond bands,
wherein each trace from the second set of conductive traces terminates at a bond pad of the plurality of bond pads,
wherein the second set of conductive traces of the adapter are in electrical contact with the first set of conductive traces, and
wherein the connector electrically connects the first set of conductive traces to the electronics module.

\* \* \* \* \*